United States Patent
Bloom et al.

(10) Patent No.: US 10,444,141 B2
(45) Date of Patent: Oct. 15, 2019

(54) SYSTEMS AND METHODS FOR TRACKING PARTICLES IN A FLUID FLOW

(71) Applicant: CareFusion 303, Inc., San Diego, CA (US)

(72) Inventors: Mark Bloom, San Diego, CA (US); Cathal Oscolai, San Diego, CA (US); David Brown, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 70 days.

(21) Appl. No.: 14/677,789

(22) Filed: Apr. 2, 2015

(65) Prior Publication Data

US 2016/0292866 A1    Oct. 6, 2016

(51) Int. Cl.
| | |
|---|---|
| *G01N 21/17* | (2006.01) |
| *H04N 5/225* | (2006.01) |
| *H04N 5/232* | (2006.01) |
| *G06T 7/246* | (2017.01) |

(52) U.S. Cl.
CPC .............. *G01N 21/17* (2013.01); *G06T 7/246* (2017.01); *H04N 5/2256* (2013.01); *H04N 5/23229* (2013.01); *G01N 2021/177* (2013.01); *G01N 2291/02433* (2013.01); *G06T 2207/10004* (2013.01); *G06T 2207/10016* (2013.01)

(58) Field of Classification Search
CPC .......... G06T 7/00; H04N 5/232; H04N 5/225; G01N 21/17
USPC ........................................................ 348/143
See application file for complete search history.

(56) References Cited

U.S. PATENT DOCUMENTS

| | | | |
|---|---|---|---|
| 5,006,110 A | 4/1991 | Garrison et al. | |
| 5,195,520 A | * 3/1993 | Schlief ...................... | A61B 8/04 424/9.52 |

(Continued)

FOREIGN PATENT DOCUMENTS

| | | |
|---|---|---|
| CN | 101528288 A | 9/2009 |
| CN | 102791310 A | 11/2012 |

(Continued)

OTHER PUBLICATIONS

Stöhr, M., C. Garbe, D. Engelmann, P. Geissler, S. Gomes, F. Hering, H.-G. Wagner and B. Jahne, 4-D particle tracking velocimetry applied to gas-liquid reactors. In Proc. Of the Int. Workshop of Scientific Computing in Chemical Engineering II, Hamburg-Harburg, 1999.*

(Continued)

*Primary Examiner* — Richard A Hansell, Jr.
(74) *Attorney, Agent, or Firm* — Mintz Levin Cohn Ferris Glovsky and Popeo, P.C.

(57) ABSTRACT

A system is described that can detect, track and analyze a bubble of a secondary substance contained within a primary substance along a part of a fluid line. For example, the system can detect the presence of the bubble within the primary substance along the part of the fluid line, which can include assigning a digital signature to the bubble. In addition, the system can track the movement of the bubble in order to ensure that the bubble is accounted for only once as it passes through the part of the fluid line. Furthermore, the system can analyze the bubble, such as determine its direction of travel, speed of travel, volume and size.

16 Claims, 6 Drawing Sheets

(56) References Cited

U.S. PATENT DOCUMENTS

| | | | | |
|---|---|---|---|---|
| 5,544,215 | A * | 8/1996 | Shroy, Jr. | A61B 6/481 |
| | | | | 348/E5.089 |
| 6,252,980 | B1 * | 6/2001 | Schwartz | G01F 23/292 |
| | | | | 382/141 |
| 7,758,811 | B2 * | 7/2010 | Durack | C12N 5/0612 |
| | | | | 422/73 |
| 8,691,584 | B2 * | 4/2014 | Durack | G01N 33/48 |
| | | | | 422/73 |
| 8,723,104 | B2 * | 5/2014 | Sun | G01N 15/1429 |
| | | | | 250/251 |
| 2002/0134134 | A1 * | 9/2002 | Derek | A61M 1/3626 |
| | | | | 73/19.03 |
| 2005/0121814 | A1 | 6/2005 | Morrison | |
| 2008/0098798 | A1 * | 5/2008 | Riley | A61M 5/365 |
| | | | | 73/19.03 |
| 2008/0200865 | A1 * | 8/2008 | Bedingfield | A61M 1/28 |
| | | | | 604/29 |
| 2010/0097451 | A1 * | 4/2010 | Bruce | A61M 5/16831 |
| | | | | 348/61 |
| 2011/0209764 | A1 * | 9/2011 | Uber | A61M 5/007 |
| | | | | 137/1 |
| 2011/0237880 | A1 | 9/2011 | Hamel et al. | |
| 2012/0045103 | A1 * | 2/2012 | Salsman | G01N 15/1012 |
| | | | | 382/128 |
| 2013/0030405 | A1 | 1/2013 | Hartman et al. | |
| 2013/0177455 | A1 * | 7/2013 | Kamen | G06F 19/3418 |
| | | | | 417/313 |
| 2013/0204227 | A1 * | 8/2013 | Bochenko | G06F 19/3456 |
| | | | | 604/506 |
| 2014/0319356 | A1 * | 10/2014 | Sartorius | G01N 21/3577 |
| | | | | 250/341.8 |
| 2015/0167045 | A1 * | 6/2015 | Brubacher | C12Q 1/04 |
| | | | | 435/288.7 |

FOREIGN PATENT DOCUMENTS

| | | |
|---|---|---|
| EP | 2368484 A1 | 9/2011 |
| WO | WO-2008/051576 A2 | 5/2008 |
| WO | WO-2014/144557 A2 | 9/2014 |

OTHER PUBLICATIONS

Stöhr publication date: screen shot taken from google search results. See attached PDF titled Stöhr publication date.*

Ohmi K., S. P. Pandy, A. Sapkota, Particle tracking velocimetry with an ant colony optimization algorithm, Exp Fluids (2010) 48:589-605 DOI 10.1007/s00348-009-0815-2.*

Stohr, M., C. Garbe, D. Engelmann, P. Geissler, S. Gomes, F. Hering, H.-G. Wagner and B. Jahne, 4-D particle tracking velocimetry applied to gas-liquid reactors. In Proc. Of the Int. Workshop of Scientific Computing in Chemical Engineering II, Hamburg-Harburg, 1999 (Year: 1999).*

Ohmi K., S. P. Pandy, A. Sapkota, Particle tracking velocimetry with an ant colony optimization algorithm, Exp Fluids (2010) 48:589-605 DOI 10.1007/S00348-009-0815-2 (Year: 2010).*

Wang, H.Y. and F. Dong (2009), "A method for bubble volume calculating in vertical two-phase flow." *Journal of Physics: Conference Series, The 6th International Symposium on Measurement Techniques for Multiphase Flows*, IOP Publishing, Bristol, GB. vol. 147, No. 1, p. 12018.

* cited by examiner

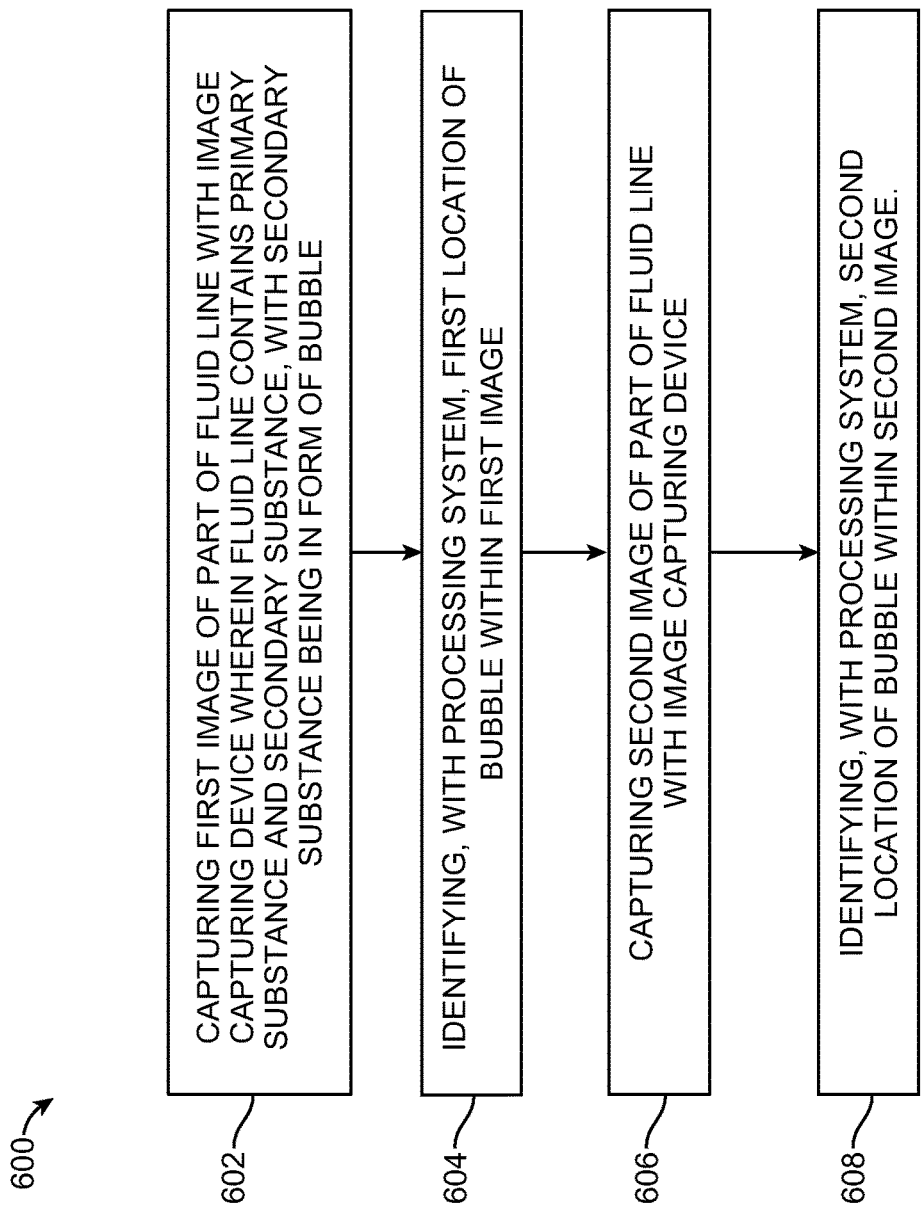

_US 10,444,141 B2_

SYSTEMS AND METHODS FOR TRACKING PARTICLES IN A FLUID FLOW

TECHNICAL FIELD

The subject matter described herein relates to a system for detecting, tracking and analyzing a secondary substance, which can be in the form of a bubble, within a primary substance contained within a fluid line.

BACKGROUND

Intravenous (IV) systems that deliver fluid to patients typically employ the use of an air-in-line (AIL) sensor that can detect air passing through a fluid line. AIL sensors are an important part of an infusion system as they alert care givers when dangerous amount of air may be passing to a patient. However, traditional AIL sensors suffer from several limitations; specifically, they are not able to detect whether an air bubble being sensed is the same air bubble that was previously sensed, and they are generally not ideal for sensing objects other than air. For example, a bubble can become trapped in a fluid line and oscillate within the fluid line. A traditional AIL sensor may be able to detect the trapped bubble, however, the traditional AIL sensor cannot distinguish a trapped air bubble and will account for the trapped air bubble more than once. This can result in incorrect calculations related to the amount of air passing through the fluid line. Also, a traditional AIL sensor is not well-suited for detecting a secondary substance that is not air, that will therefore be less likely be able to alert a care giver of a non-air secondary substance within the primary substance.

SUMMARY

Aspects of the current subject matter can include systems for tracking secondary substances, which can be in the form of a bubble, in a fluid line. In one aspect, the system an include a light source positioned adjacent the fluid line for directing light to a part of the fluid line and an image capturing device positioned adjacent the fluid line and configured to capture a first image of the part of the fluid line. The system can further include a processing system configured to process the first image for detecting a secondary substance within a primary substance, wherein the secondary substance is in the form of a bubble.

In some variations, one or more of the following features can optionally be included in any feasible combination. In some embodiments, the processing system can be configured to create a digital signature of the bubble, with the digital signature identifying an outline of the bubble that is used to track and analyze the bubble. In addition, the processing system can be further configured to identify a first location of the bubble within the first image. The image capturing device can be configured to capture a second image of the part of the fluid line and the processing system can be configured to analyze the second image and identify a second location of the bubble within the second image. The processing system can be further configured to calculate a distance between the first location and the second location and determine if the distance is within a predetermined range, wherein the predetermined range is dependent upon a fluid flow rate within the fluid line. Additionally, the image capturing device can be one or more of a digital camera, an infrared camera, and a video camera. Furthermore, the light can include infrared light and the image capturing device can be positioned at an angle from the light source relative to the fluid line.

In some embodiments of the system, the image capturing device can be positioned in line with the light source and the system can further include a background positioned on an opposite side of the fluid line from the image capturing device and light source. The processing system can be further configured to identify a refraction of the light through at least one of the primary substance and the secondary substance. The frame rate of the image capturing device can be based on the fluid flow rate. The processing system can be further configured to determine a property of the bubble, wherein the property includes one or more of a speed of travel, a direction of travel, a volume, a size, and a type of substance comprising the bubble.

In another aspect, a method of the system can include capturing a first image of a part of a fluid line containing a primary substance with an image capturing device and determining whether the fluid line contains a secondary substance, with the secondary substance being in the form of a bubble. In addition, the method can include identifying, with a processing system, a first location of the bubble within the first image and capturing a second image of the part of the fluid line with the image capturing device. Additionally, the method can include identifying, with the processing system, a second location of the bubble within the second image.

In some variations of the method, one or more of the following can optionally be included. For example, the method can further include calculating a distance between the first location and the second location. In addition, the method can include comparing the calculated distance with a predetermined range, wherein the predetermined range is dependent on a flow rate within the fluid line. Additionally, the method can include adjusting a frame rate of the image capturing device based on the comparison of the calculated distance with the predetermined range. Furthermore, the method can include analyzing the bubble in at least one of the first image and the second image in order to determine a property of the bubble, wherein the property includes one or more of a speed of travel, a direction of travel, a volume, a size, and a type of substance comprising the bubble. The method can further include illuminating a part of a fluid line with light from a light source.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 6 shows a process flow diagram illustrating aspects of a method having one or more features consistent with implementations of the current subject matter.

When practical, similar reference numbers denote similar structures, features, or elements.

DETAILED DESCRIPTION

Figure 1:
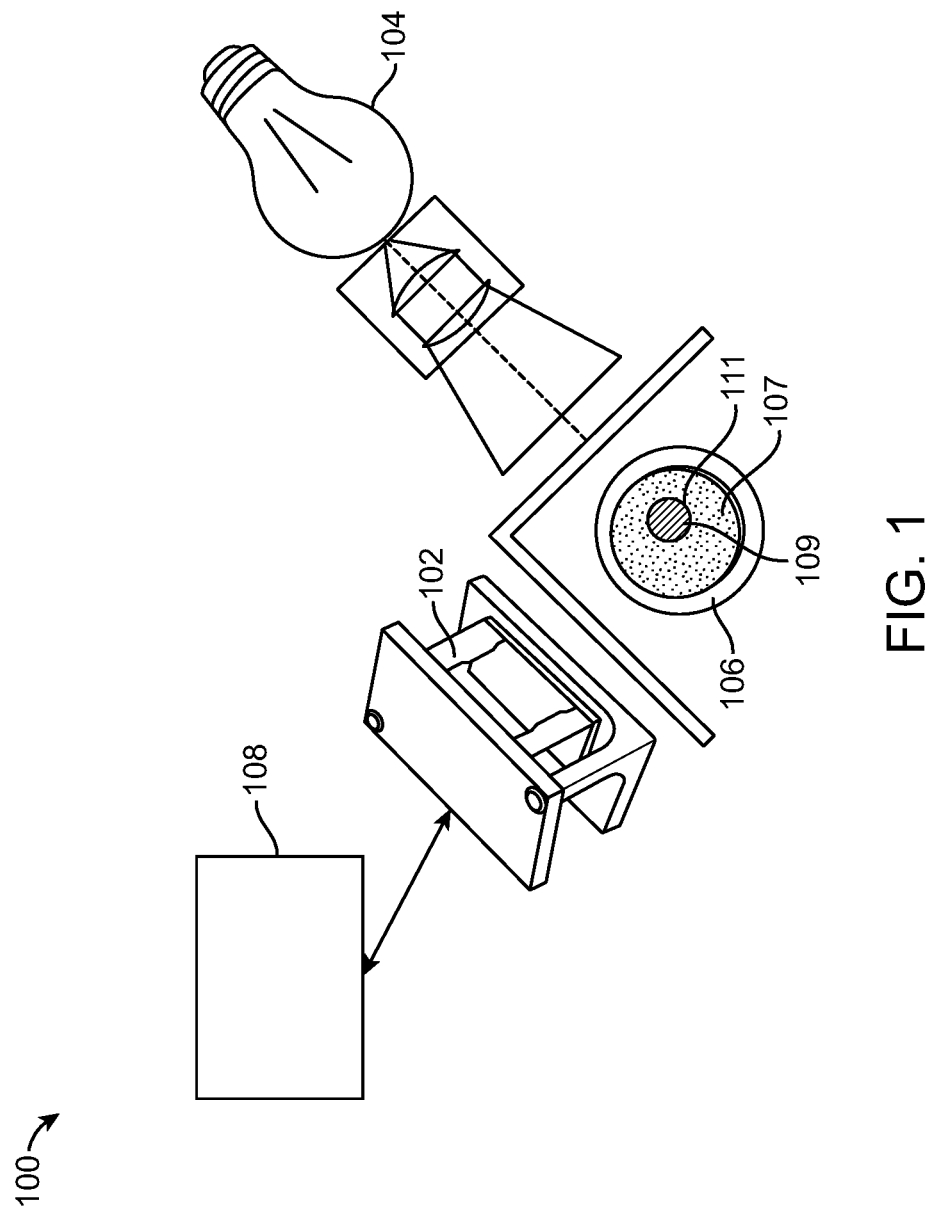
FIG. 1 shows an implementation of a bubble tracking system, including an image capturing device and a light source positioned adjacent a fluid line.

The current subject matter is directed to a system that can detect, track and analyze a secondary substance (e.g., air) contained within a primary substance (e.g., saline solution) along a part of a fluid line. For example, the system can detect and identify the presence of an air bubble within the primary substance, which can also include assigning a digital signature to the bubble. In addition, the system can track the movement of the bubble in order to ensure that the bubble is accounted for only once as it passes through the fluid line. Furthermore, the system can analyze the bubble, such as determine its direction of travel, speed of travel, volume, size, etc. The system can also detect density differences between the primary and secondary fluids which enables the system to determine with a secondary infusion has finished and when a primary infusion begins. The system can improve the accuracy of measuring an amount of a secondary substance that passes through the fluid line by implementing improved systems, methods and devices for detecting, tracking and analyzing the secondary substance, as will be described in greater detail below.

For example, the system can provide improved ways in which to detect, track and analyze how much secondary substance, such as air (i.e., air bubbles), passes through a defined potion of the fluid line and moving in a path toward a patient. This can allow a device or system that delivers a primary fluid (e.g., saline solution) to a patient to efficiently and effectively keep track of how much air is passes through the fluid line and is believed to be delivered to a patient. It can be important to keep track of the amount of air that a patient receives through an IV line to ensure that the patient is not at risk for an air embolism, which can cause medical complications (e.g., heart attack, stroke, etc.).

In some traditional AIL sensors it can be difficult to keep an accurate account of how many bubbles or how much air is delivered to the patient. For example, bubbles can get trapped and oscillate in the fluid line, which can cause, for example, AIL sensors to account for a single bubble more than once. Also, some current AIL sensors are not able to detect small volume bubbles of a secondary substance. For example, some current AIL sensors cannot detect volumes that are less than 30 microliters. As a result, these AIL sensors can create false alarms as to an amount of air that has passed through the fluid line, which can interrupt therapy and unnecessarily prolong and complicate treatment of a patient, or they can create an inaccurate measurement of the amount of air that has passed through the fluid line, potentially endangers the patient. In contrast, the present system described herein provides systems and methods for tracking individual bubbles along a fluid path in order to ensure that each bubble is accounted for only once. In addition, measurements of each bubble can be made with system that allows the system to determine an amount of the secondary substance (e.g., air) in each bubble, as well as efficiently and effectively calculate a total amount of the secondary substance that passes through the fluid line. This information can be used in order to calculate accurate amounts of secondary substance that is delivered to the patient and provide accurate information to caretakers and patients, such as warnings as to the amount of secondary substance that has been or will be delivered to the patient.

As will be discussed in greater detail below, the system can identify and calculate any number of features related to the secondary substance, such as direction of movement, volume, speed, merging of bubbles, dividing of bubbles, etc. Furthermore, the system can track one or more bubbles simultaneously and can detect more than two substances (i.e., more than just the primary substance and secondary substance). Therefore, although examples discussed herein may reference a single bubble or a primary substance and/or a secondary substance, the system is not limited to such examples.

Some implementations of the system can include an image capturing device and a light source, with both the image capturing device and light source positioned adjacent the fluid line. The fluid line can contain fluid (e.g., primary and secondary substances) that can be captured by the image capturing device with the assistance of the light source illuminating a part of the fluid line. A processing system can process images captured by the image capturing device in order to determine the presence of either a primary substance or a secondary substance (which can be in the form of bubbles). In addition, the captured images can be processed by a processing system in order to track individual bubbles as well as determine properties associated with each of the bubbles (e.g., direction of travel, speed of travel, oscillation, volume, size, etc.). The image capturing device can capture multiple frames of the bubble passing through the fluid line at a rate such that the bubble will never move farther than its diameter from one frame to the next. In this manner the system is able to track the bubble from one frame to the next and is able to reliably and consistently determine the direction, speed and general movement of the bubble.

FIG. 1 illustrates an implementation of a system 100 that includes an image capturing device 102 and a light source 104 positioned adjacent a fluid line 106. For example, the fluid line 106 can be in fluid communication with a part of an infusion system or device that delivers a primary substance 107 (e.g., water) to a patient. The system 100 can be configured to efficiently and effectively detect, track, and analyze one or more secondary substances 109 (e.g., air) contained within the primary substance 107, which can travel in the form of a bubble 111. This can assist with ensuring that an unsafe volume of the secondary substance 109 is not delivered to the patient. Although examples and implementations are described herein relating to a primary substance 107 and a secondary substance 109, any number of substances can be detected, tracked and analyzed with the system 100. In addition, although bubbles are described in examples as being detected, tracked, and analyzed using the system 100, the system 100 can detect any number of substances (e.g., foreign materials) in any number of shapes or formations.

The light source 104 can provide one or more of a variety of types of light, such as infrared light, which can illuminate the part of fluid line 106 the image capturing device 102 is positioned to capture. In addition, the light from the light source 104 can assist the image capturing device 102 with capturing properties associated with primary substance 107 and secondary substance 109, such as allowing the image capturing device 102 to capture reflective and/or refractive properties of the primary substance 107 and/or secondary substance 109. This can assist a processing system 108 associated with the system 100 to process images captured by the image capturing device 102 in order to detect, track and analyze bubbles 111 in the fluid line 106.

The light source 104 can be any of a variety of light sources, such as an infrared light source. Additionally, more than one light source 104 can be used for lighting various angles and/or positions along the fluid line 106. The light delivered from the light source 104 can be analyzed by the processing system 108 and/or image capturing device 102. For example, the refraction of the light as it passes through either the primary substance 107 or the secondary substance 109 can assist the system 100 with detecting the presence of either the primary substance 107 or the secondary substance 109, as well as identifying the location of a bubble 511 of secondary substance 109. Furthermore, this information can be used by the processing system 108 to assist with creating a digital signature of the bubble 111.

The image capturing device 102 can include a digital camera, an infrared camera, or a video camera. In addition, the image capturing device 102 can be positioned in a variety of positions relative to either the fluid line 106 or the light source 104. As shown in FIG. 1, the image capture device 102 can be positioned at an angle, such as a 90 degree angle, from the light source 104 relative to the fluid line 106. In addition, some implementations of the system 100 can include more than one image capturing device 102, such as for capturing various angles and/or positions along the fluid line 106.

Figure 2:
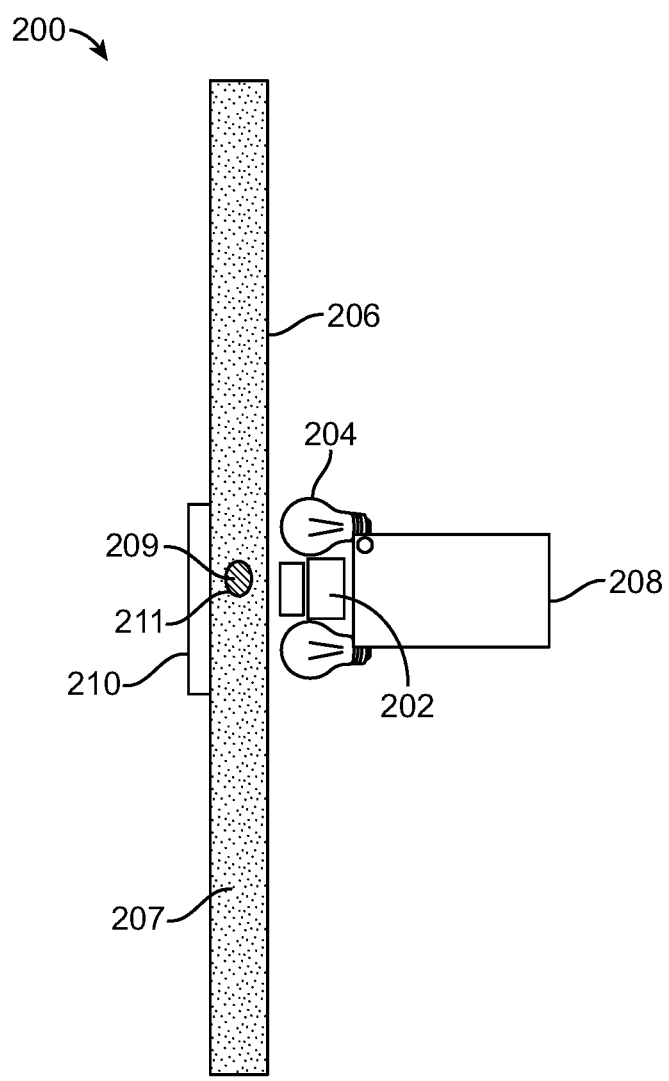
FIG. 2 shows another implementation of a bubble tracking system, which includes the image capturing device positioned in line with the light source.

FIG. 2 shows another implementation of a system 200, which can include an image capturing device 202 positioned in line with a light source 204 adjacent to a fluid line 206. In addition, the system 200 can include a background 210, such as a dark (e.g., black) background, positioned on an opposite side of the fluid line 206 from the image capturing device 202 and light source 204. The background 210 can assist with cutting out background light, which can allow for clearer images to be captured by the image capturing device 202. The background 210 also enables the system to filter out inconsistencies with the image capturing device 202 and enables the calibration of the image capturing device 202 in order to effectively operate with multiple types of tubing.

Figure 3:
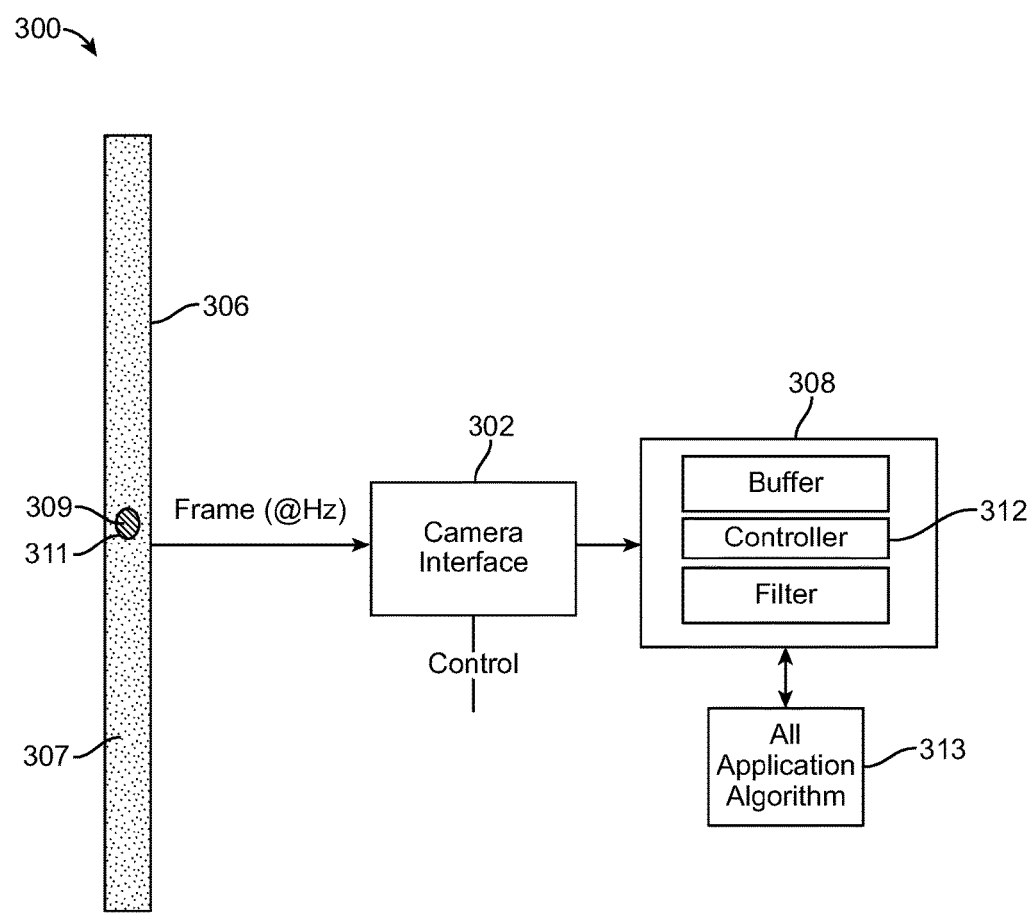
FIG. 3 shows an implementation of a processing system of the bubble tracking system, with the processing system being configured to process the images captured by the image capturing device for detecting, tracking and analyzing at least one substance contained in the fluid line.

FIG. 3 shows an implementation of a system 300 including a processing system 308 configured to process images captured by the image capturing device 302 for detecting, tracking and analyzing bubbles 311 of a secondary substance 309 contained within a primary substance 307. For example, the processing system 308 can include a controller 312 for controlling the image capturing device 302, such as the rate at which the image capturing device 302 captures images (i.e., frame rate). The frame rate can be set or adjusted by the controller 312 based on a fluid flow rate within the fluid line 306. For example, if the flow rate within the fluid line 306 increases, the controller 312 can increase the frame rate. This can allow the image capture device 302 to capture enough images of the fluid line 306 such that each bubble 311 of the secondary substance 309 can be detected, tracked and analyzed. By way of further example, if the flow rate within the fluid line 306 decreases, the controller 312 can decrease the frame rate. The frame rate can be set or adjusted to ensure that fluid flowing within the fluid line 306, including any bubbles 311, is captured in at least one image by the image capturing device 302, which can allow the processing system 308 to analyze each of the bubbles 311 that flow through the fluid line.

The processing system 308 can further include an algorithm 313 that can assist with processing the images captured by the image capturing device 302. For example, the algorithm 313 can assist with determining a location of the bubble 311 captured by the image capturing device 314. In addition, the algorithm 313 can assist with creating a digital signature of the bubble 311, which can assist with tracking the bubble 311 in subsequent images. The digital signature can define an outline and/or size of the bubble, which can be determined based on a refraction of light through the bubble 311 that can be detected by either the image capturing device 302 or the processing system 308, such as the algorithm 313. Additionally, the algorithm 313 can assist with determining an approximate size and/or volume of the bubble 311, which can be used by the system 300 to keep track of how much (i.e., volume) of the secondary substance 309 is being, or has been, delivered to the patient. Although the processing system is described by way of example, as having a single algorithm, the processing system can have more than one algorithm.

Figure 4A:
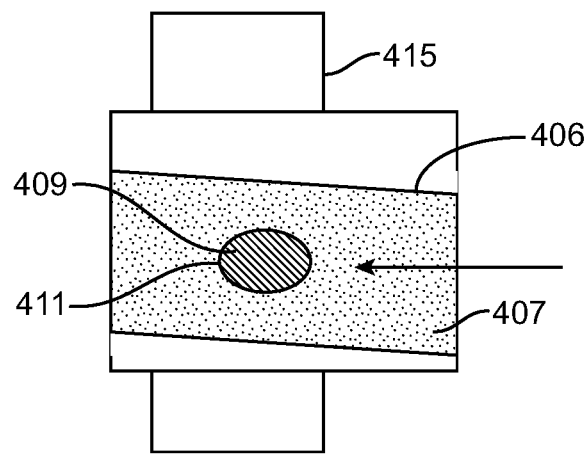
FIG. 4A shows an example of a bubble of a secondary substance in a first position within a part of the fluid line.

FIG. 4A shows an example of a bubble 411 of a secondary substance 409 in a first position within a part of the fluid line 406. The first position can be referenced based on an acquisition window or frame 415 of a captured image taken by the image capturing device 102. The frame 415 can be the same location along the fluid line 406 for each image captured by the image capturing device 102. As such, the frame 415 can be used as a reference point for locating and tracking bubbles 411 captured within each image.

Figure 4B:
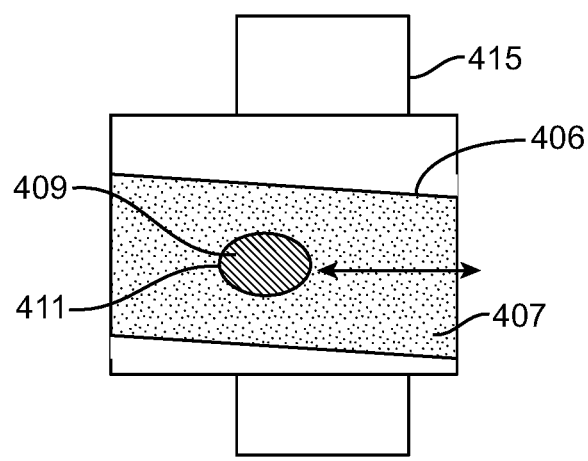
FIG. 4B shows an example of the bubble of FIG. 4A in a second position within the part of the fluid line.

FIG. 4B shows an example of the bubble 411 shown in FIG. 4A, but in a second position within the frame 415. The processing system 108 can assist with locating and identifying the first position and the second position of the bubble 411 within the frame 415 for each image, as well as compare the first position and second position in order to determine characteristics of the bubble, such as what direction the bubble 411 is traveling (including back and forth or oscillating movements) and the speed at which the bubble 411 is traveling. The processing system 108 can also assign a digital signature to the bubble 411 in order to assist with tracking the location and movements of each bubble 411. Furthermore, the processing system 108 can use the digital signature to determine any number of features associated with the bubble 411, such as the size and volume of each bubble 411, or when a bubble splits apart or coalesces.

Figure 5:
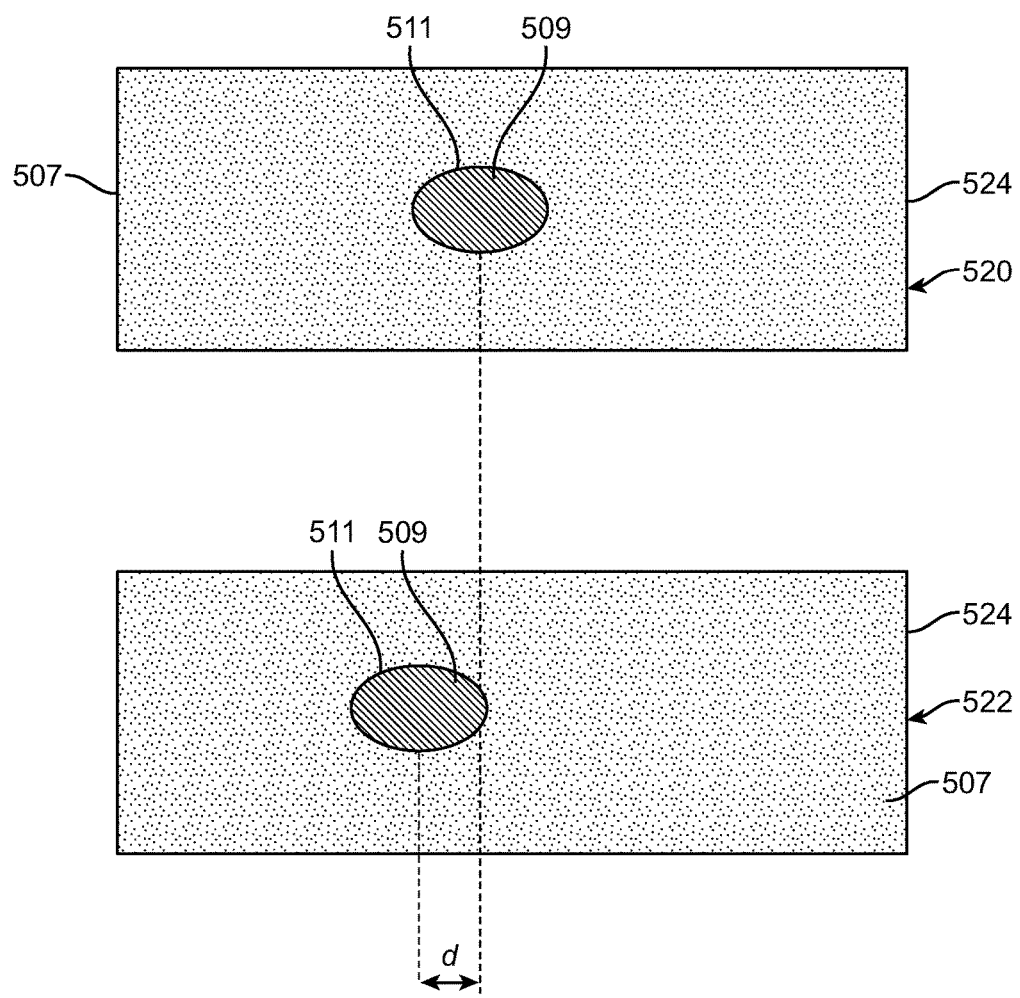
FIG. 5 shows an example of a first image and a second image taken by the image capturing device that are analyzed by the processing system in order to detect, track and analyze at least the bubble of secondary substance within the fluid line.

FIG. 5 shows an example of a first image 520 and a second image 522 taken by the image capturing device 102 that can be processed by the processing system 108 in order to detect, track and analyze at least the bubble 511 of secondary substance 509 within the fluid line. The first image 520 can have the same frame 524 as the second image 522 such that the frame 524 can provide a reference for the processing system 108 to identify a first position of the bubble 511 within the first image 520 and a second position of the bubble 511 within the second image 522. The processing system 108 can then calculate a distance (d) between the first position and the second position of the bubble 511. This calculated distance (d) can be compared against a predetermined range the bubble could travel, which can be based on a fluid flow rate in the fluid line.

For example, the predetermined range can indicate a minimum and maximum distance the bubble 511 can travel given the flow rate of fluid within a part of the fluid line 106. As such, if the calculated distance (d) is outside of the predetermined range, then the processing system 108 can determine that more than one bubble traveled past the part of the fluid line. However, if the calculated distance (d) is within the predetermined range, then the processing system 108 can determine, along with other indications (e.g., digital signature of the bubble), that the same bubble is being tracked. Additional features associated with the processing system 108 can also assist with detecting and tracking each bubble 511, such as the digital signature assigned to each bubble. The digital signature can assist in keeping track of each bubble 511 and ensure that each bubble 511 is counted only once. This can ensure that even bubbles that oscillate and/or get trapped within the fluid line 106 are not repeatedly accounted for, which can create false information (e.g., false alarms). The digital signature can also assist in tracking each bubble 511, including during merging of two or more bubbles and/or dividing of one or more bubbles.

In some implementations, the detection and identification of properties associated with either the primary substance or the secondary substance, including properties associated with the bubble, can be based on a total internal reflection ("TIR") principle derived from Snell's Law and the Fresnel Equations. For example, the TIR principle can specify the relative amount of light reflected and transmitted by a surface and can assist with describing the behavior of light, such as from the light source 104, as it passes the surface between two media (e.g., primary and secondary substances) with different refraction indices. The TIR principal can be included in some of the processing associated with the processing system, such as included in an algorithm for determining a property of either the primary substance or secondary substance (e.g., type of substance, outline or size of substance, etc.).

FIG. 6 shows a process flow chart 600 illustrating features of a method consistent with one or more implementations of the current subject matter. It will be understood that other implementations may include or exclude certain features. At 602, a first image of a part of the fluid line can be captured with an image capturing device. The fluid line can contain a primary substance and a secondary substance, with the secondary substance being in the form of a bubble. Then, at 604, the processing system can identify a first location of the bubble within the first image. At 606, the image capturing device can capture a second image of the part of the fluid line. Then, at 608 the processing system can identify a second location of the bubble within the second image.

Furthermore, the processing system can also calculate a distance between the first location and the second location of the bubble and determine whether the calculated distance is within a predetermined range. The predetermined range can be dependent upon a flow rate within the fluid line. The frame rate of the image capturing device can be adjusted based on the whether the calculated distance is within the predetermined range. In addition, the processing system can analyze the bubble in either the first image or second image in order to determine one or more of a speed of travel of the bubble, a direction of travel of the bubble, a volume of the bubble, a size of the bubble, and a type of substance comprising the bubble. The method can further include illuminating a part of the fluid line with light from a light source and positioning the image capturing device in various positions relative to the light source and fluid line.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. A system for tracking bubbles in a patient fluid line of an intravenous system that delivers fluid to a patient, comprising:

a light source positioned adjacent the fluid line for directing light to a part of the fluid line, wherein the fluid line is intravenously connected to a patient and contains a primary substance flowing toward and into a patient;

an image capturing device positioned adjacent the fluid line and configured to capture a first image and capture a second image of the part of the fluid line that contains the primary substance flowing toward and into the patient;

a controller configured to adjust a frame rate of the image capturing device based on an actual fluid flow rate of the primary substance in the fluid line; and a processing system configured to:

process the first image for detecting a secondary substance within the primary substance, wherein the secondary substance is in the form of a bubble;

create a digital signature of the bubble, with the digital signature identifying an outline of the bubble that is used to track and analyze the bubble;

identify a first location of the bubble within the first image;

analyze the second image and identify a second location of the bubble within the second image;

calculate a distance between the first location and the second location and determine if the distance is within a predetermined range, wherein the predetermined range indicates a minimum and maximum distance the bubble is able to travel given the flow rate of fluid within the part of the fluid line;

determine that more than one bubble traveled past the part of the fluid line if the calculated distance is outside of the predetermined range;

determine, along with the digital signature of the bubble, that the same bubble is being tracked if the calculated distance is within the predetermined range and wherein the controller further adjusts the frame rate such that the bubble does not move farther than a diameter of the bubble from the first image to the second image.

2. The system of claim 1, wherein the image capturing device is one or more of a digital camera, an infrared camera, and a video camera.

3. The system of claim 1, wherein the light comprises infrared light.

4. The system of claim 1, wherein the image capturing device is positioned at an angle from the light source relative to the fluid line.

5. The system of claim 1, wherein the image capturing device is positioned in line with the light source and system further includes a background positioned on an opposite side of the fluid line from the image capturing device and light source.

6. The system of claim 1, wherein the processing system is further configured to identify a refraction of the light through at least one of the primary substance and the secondary substance.

7. The system of claim 1, wherein the processing system is further configured to determine a property of the bubble, wherein the property includes one or more of a speed of travel, a direction of travel, a volume, a size, and a type of substance comprising the bubble.

8. A method of tracking air flow in an intravenous fluid delivery system that delivers fluid to a patient, comprising:

intravenously connecting a fluid line to the patient;

causing a primary substance to flow toward and into a patient through the fluid line;

adjusting, by a controller, a frame rate of an image capturing device based on an actual flow rate of the primary substance in the fluid line as the primary substance flows toward and into the patient;

capturing a first image of a part of the fluid line containing the primary substance with the image capturing device;

determining whether the fluid line contains a secondary substance, with the secondary substance being in the form of a bubble;

creating a digital signature of the bubble, with the digital signature identifying an outline of the bubble that is used to track and analyze the bubble;

identifying, with a processing system, a first location of the bubble within the first image;

capturing a second image of the part of the fluid line with the image capturing device;

further adjusting the frame rate such that the bubble does not move farther than a diameter of the bubble from the first image to the second image;

identifying, with the processing system, a second location of the bubble within the second image;

calculating, with the processing system, a distance between the first location and the second location;

comparing, with the processing system, the calculated distance with a predetermined range, wherein the predetermined range indicates a minimum and maximum distance the bubble is able to travel given the flow rate of fluid within the part of the fluid line;

determining that more than one bubble traveled past the part of the fluid line, if the calculated distance is outside of the predetermined range; and determining, along with the digital signature of the bubble, that the same bubble is being tracked, if the calculated distance is within the predetermined range.

9. The method of claim 8, further comprising calculating a distance between the first location and the second location.

10. The method of claim 9, further comprising comparing the calculated distance with a predetermined range, wherein the predetermined range is dependent on the actual flow rate within the fluid line.

11. The method of claim 10, further comprising adjusting a frame rate of the image capturing device based on the comparison of the calculated distance with the predetermined range.

12. The method of claim 8, further comprising analyzing the bubble in at least one of the first image and the second image in order to determine a property of the bubble, wherein the property includes one or more of a speed of travel, a direction of travel, a volume, a size, and a type of substance comprising the bubble.

13. The method of claim 8, further comprising illuminating a part of a fluid line with light from a light source.

14. The method of claim 13, wherein the image capturing device is positioned at an angle from the light source relative to the fluid line.

15. The method of claim 13, wherein the image capturing device is positioned in line with the light source and the bubble tracking system further includes a background positioned on an opposite side of the fluid line from the image capturing device and light source.

16. The system of claim 1, wherein the controller adjusts the frame rate of the image capturing device to increase based on an increase in the actual fluid flow rate, and the controller adjusts the frame rate of the image capturing device to decrease based on a decrease in the actual fluid flow rate.

* * * * *